(12) United States Patent
Richmond et al.

(10) Patent No.: US 8,293,520 B2
(45) Date of Patent: *Oct. 23, 2012

(54) ANIMAL CELL COLONY PICKING APPARATUS AND METHOD

(75) Inventors: Stephen Richmond, Christchurch (GB); Christopher Mann, Barton-on-Sea (GB); Andrew Board, Wimborne (GB); Yonggang Jiang, New Milton (GB)

(73) Assignee: Molecular Devices (New Milton) Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/267,707

(22) Filed: Oct. 6, 2011

(65) Prior Publication Data

US 2012/0028239 A1 Feb. 2, 2012

Related U.S. Application Data

(62) Division of application No. 12/318,612, filed on Jan. 2, 2009, now Pat. No. 8,034,612, which is a division of application No. 10/631,845, filed on Aug. 1, 2003, now Pat. No. 7,776,584.

(51) Int. Cl.
C12M 1/26 (2006.01)
C12M 3/00 (2006.01)
C12M 1/34 (2006.01)

(52) U.S. Cl. ............... 435/286.3; 435/309.1; 435/288.7; 435/309.3; 435/287.3; 435/308.1; 435/309.4; 73/864.01; 73/864.11; 73/864.24; 362/133

(58) Field of Classification Search ............... 435/309.1, 435/286.3, 288.7, 309.3, 287.3, 308.1, 309.4; 73/864.01, 864.11, 864.24; 362/133
See application file for complete search history.

(56) References Cited

U.S. PATENT DOCUMENTS

| 4,210,724 A | 7/1980 | Sogi et al. |
| 4,481,298 A | 11/1984 | Cone et al. |
| 4,700,298 A | 10/1987 | Palcic et al. |

(Continued)

FOREIGN PATENT DOCUMENTS

DE 19742163 4/1999

(Continued)

OTHER PUBLICATIONS

Office Action for related U.S. Appl. No. 11/401,966, dated Feb. 19, 2009.

(Continued)

*Primary Examiner* — Nathan Bowers
(74) *Attorney, Agent, or Firm* — James R. Abney; Bella Fishman

(57) ABSTRACT

Animal cell colonies are picked up automatically by an apparatus having a picking head with a plurality of hollow pins and an integrated imager for capturing an image of adherent or non-adherent animal cell colonies held in liquid or semi-solid medium. Image processing identifies the locations of the animal cell colonies to be picked. Picking an animal cell colony is performed by aligning each of the hollow pins in turn with a target animal cell colony location, introducing the hollow pin into the medium, and aspirating the animal cell colony into the hollow pin. In the case of an adherent colony, the distal end of the pin is forced into oscillation to detach the animal cell colony prior to aspiration. The animal cell colony is dispensed into a well plate by increasing pressure in the fluid conduit.

19 Claims, 10 Drawing Sheets

U.S. PATENT DOCUMENTS

| | | | |
|---|---|---|---|
| 4,950,592 | A | 8/1990 | Daiss |
| 5,125,748 | A | 6/1992 | Bjornson et al. |
| 5,491,084 | A | 2/1996 | Chalfie et al. |
| 5,534,386 | A | 7/1996 | Petersen et al. |
| 5,587,062 | A | 12/1996 | Togawa et al. |
| 5,764,807 | A | 6/1998 | Pearlman et al. |
| 6,064,754 | A * | 5/2000 | Parekh et al. ............... 382/129 |
| 6,146,881 | A * | 11/2000 | Hering ..................... 435/284.1 |
| 6,198,107 | B1 | 3/2001 | Seville |
| 6,278,794 | B1 | 8/2001 | Parekh et al. |
| 6,379,918 | B1 | 4/2002 | Feldsine et al. |
| 6,509,166 | B1 | 1/2003 | Edberg |
| 6,673,614 | B2 | 1/2004 | Charlton et al. |
| 6,790,636 | B1 | 9/2004 | Star et al. |
| 7,105,129 | B2 | 9/2006 | Ruddock |
| 2002/0019009 | A1* | 2/2002 | Roggen et al. ............... 435/7.1 |
| 2002/0068045 | A1 | 6/2002 | Reubinoff et al. |
| 2003/0132109 | A1 | 7/2003 | Bullen et al. |
| 2003/0179916 | A1* | 9/2003 | Magnuson et al. ........... 382/128 |
| 2004/0096984 | A1 | 5/2004 | Elverd et al. |
| 2005/0070011 | A1* | 3/2005 | Kuzan et al. ............... 435/287.2 |
| 2005/0118652 | A1 | 6/2005 | Lee et al. |
| 2007/0025880 | A1 | 2/2007 | Hoummady |

FOREIGN PATENT DOCUMENTS

| | | | |
|---|---|---|---|
| EP | 0293649 | | 12/1998 |
| GB | 2310006 | A * | 8/1997 |
| JP | 7260742 | | 10/1995 |
| WO | 9212233 | | 7/1992 |
| WO | 9823950 | | 6/1998 |
| WO | 9951977 | | 10/1999 |
| WO | 0132834 | | 5/2001 |
| WO | 03179916 | | 9/2003 |

OTHER PUBLICATIONS

Cetonimate Product Brochure, dated Nov. 20, 2002, 2 pgs.

OTZ Newspaper Article dated Apr. 10, 2003, 2 pgs (English Translation of relevant parts attached).

Jones et al., "Integration of Image Analysis and Robotics Into a Fully Automated Colony Picking and Plate Handling System," Nucleic Acids Research, vol. 20, No. 17, 1992 Oxford University Press, Cambridge, U.K., pp. 4599-4606.

Uber et al, "Application of Robotics and Image Processing to Automated Colony Picking and Arraying," Biotechniques, vol. 11, No. 5, 1991, pp. 642-646.

Office Action for related U.S. Appl. No. 12/318,612, dated Nov. 5, 2010.

Office Action for related U.S. Appl. No. 10/631,845, dated Nov. 12, 2009.

Office Action for related U.S. Appl. No. 10/631,845, dated Feb. 3, 2009.

Office Action for related U.S. Appl. No. 12/318,612, dated Mar. 22, 2011.

Bronstein et al., "Chemiluminescense: Sensitive Detection Technology for Reporter Gene Assays," Clinical Chemistry, vol. 42, No. 9, 1996, pp. 1542-1546.

Bronstein et al., "Chemiluminescent and Bioluminescent Reporter Gene Assays," Analytical Chemistry, vol. 219, 1994, pp. 169-181.

Chalfie et al., "Green Fluorescent Protein as a Marker for Gene Expression," Science, vol. 263, Feb. 11, 1994, pp. 802-805.

Johnson et al., "Introduction to the Bioluminescence of Medusae, with Special Reference to the Photoprotein Aequorin," Methods in Enzymology, vol. 57, 1978, pp. 271-291.

Morise et al., "Intermolecular Energy Transfer in the Bioluminescent System," Biochemistry, vol. 13, No. 12, 1974, pp. 2656-2662.

Rizzuto et al., "Chimeric Gree Fluorescent Protein as a Tool for Visualizing Subcellular Organelle in Living Cells," Current Biology, vol. 5, No. 6, 1995. pp, 635-642.

van Roessel et al., "Imaging Into the Future: Visualizing Gene Expression and Protein Interactions With Fluorescent Proteins," Nature Cell Biology, vol. 4, Jan. 2002, pp. E15-E20.

Ward et al., "Spectrophotometric Identity of the Energy Transfer Chromophores in Renilla and Aequorea Gree-Fluorescent Proteins," Photochemistry and Photobiology, vol. 31, 1980, pp. 611-615.

Notice of Allowance related to U.S. Appl. No. 10/631,845, dated May 7, 2010.

* cited by examiner

ANIMAL CELL COLONY PICKING APPARATUS AND METHOD

CROSS-REFERENCE TO RELATED APPLICATIONS

This patent application is a divisional of a co-pending U.S. application Ser. No. 12/318,612 filed on Jan. 2, 2009 being a divisional application of U.S. application Ser. No. 10/631,845 filed on Aug. 1, 2003 and issued as a U.S. Pat. No. 7,776,584 that are incorporated herein by references in their entirety.

BACKGROUND OF THE INVENTION

The invention relates to an apparatus and method for picking mammalian and other animal

SUMMARY OF THE INVENTION

According to a first aspect of the invention there is provided an apparatus for picking animal cell colonies comprising: an apparatus bed for arranging a sample container comprising a plurality of animal cell colonies held in a medium; a camera for capturing images of the animal cell colonies; image processing software for identifying animal cell colony locations from captured images; and a picking head movable around the apparatus bed using positioning motors to animal cell colony locations identified by the image processing software, wherein the picking head comprises a plurality of hollow pins connected through fluid conduits to a pressure controller that is operable to aspirate quantities of medium from the sample container into the hollow pins, to retain the medium and to expel it when required, thereby allowing animal cell colonies to be picked from the medium.

According to a second aspect of the invention there is provided a method for automated picking of animal cell colonies using an apparatus, preferably according to the first aspect of the invention, comprising:
a) providing a picking head comprising a plurality of hollow pins, the picking head being movable over the apparatus using positioning motors;
b) placing a sample container including a plurality of animal cell colonies held in a medium onto the apparatus, and also a dispensing container;
c) using machine vision and image processing to identify animal cell colony locations in the sample;
d) moving the picking head to above the sample container;
e) picking an animal cell colony by aligning one of the hollow pins with one of the animal cell colony locations, introducing a distal end of the hollow pin into the medium, and aspirating the animal cell colony at that location into the hollow pin; and
f) dispensing the picked animal cell colony by moving the picking head to above the dispensing container and expelling the picked animal cell colony into the dispensing container.

The automated process can be used to sort or pick animal cell colonies which comprise, express or secrete a biological molecule, such as a protein or carbohydrate of interest, that may be detected using cell imaging. The animal cell colonies may be detected optically in a variety of ways, for example with the aid of fluorescence stains, non-fluorescent stains, or without any stains; by using Raman scattering, by using phase contrast or Nomaski interference imaging.

The colonies will most usually be mammalian cell colonies, but other animal cell colonies, such as insect cell colonies could also be picked. The target animal cell colonies can be discriminated on the basis of a variety of attributes, such as shape, size, color or molecular content that may be within the cell, in the membrane or secreted, or by any combination of multiple attributes.

The picking step may comprise repeating the aligning and aspirating steps for multiple ones of the hollow pins to pick multiple ones of the animal cell colonies.

The dispensing container may comprise an array of wells separated by a characteristic spacing in which case it is preferred that the hollow pins are also arranged with the characteristic spacing so that the expelling step can be performed in parallel for all the hollow pins. It is convenient if the hollow pins are arranged in a characteristic spacing matched to a well plate standard spacing in order to reduce head motion and also to allow the process to be parallelized.

The animal cell colonies may be contacted with or express a fluorescent protein (FP), e.g. green fluorescent protein (GFP), to assist the image processing. The FP may be within the cells, on the surface of the cells, or secreted into the medium surrounding the colony. The process can be based on any molecule that is detectable with an antibody, ligand or receptor.

The picking head can advantageously further comprise a drive mechanism for causing lateral oscillation of distal ends of the pins to facilitate detachment of adherent animal cell colonies. For example, the drive mechanism can be configured to cause rotary motion of the distal ends of the pins. Other types of motion, such as linear, would also be possible.

BRIEF DESCRIPTION OF THE DRAWINGS

For a better understanding of the invention and to show how the same may be carried into effect reference is now made by way of example to the accompanying drawing which show.

DETAILED DESCRIPTION

Figure 1:
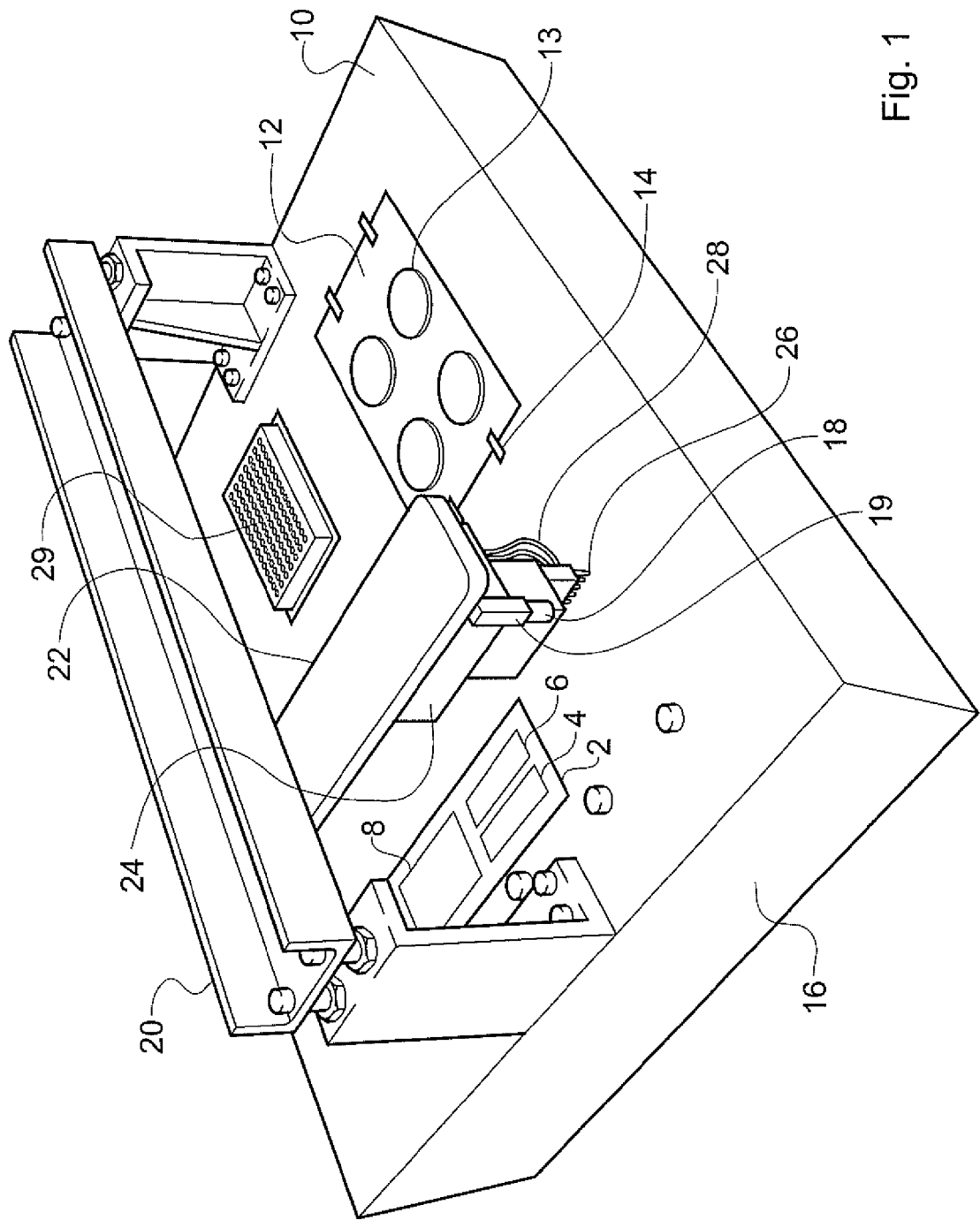
FIG. 1 is a perspective view of the lower part of an apparatus embodying the invention.

FIG. 1 is a perspective view of the lower part of an apparatus embodying the invention. The upper part is not shown in order to reveal the main bed 10 of the apparatus. A light table plate 12 made of a translucent material, known as opal acrylic, is mounted flush with the main bed. The light table plate could be made of other translucent acrylic or glass material, for example shot-blasted glass or perspex.

A set of pegs or clamps 14 (four in the figure) is provided around the periphery of the light table plate 12 for locating and securing biological sample containers containing cell colonies, such as Petri dishes 13, on the light table. The colonies could also be provided in Q-trays, omni-trays or any other suitable container. The light table plate 12 is illuminated from below by optical equipment accommodated under the main bed in the space provided in the apparatus's main base 16.

The animal cell colonies may be human cell colonies or other mammalian cell colonies, or insect cell colonies. The cells may be immortal, embryonic or stem cells, for example. Typically, the cell colonies will be grown in tissue culture.

The apparatus has a mammalian cell colony picking head 18 which is movable over the main bed of the apparatus by x-, y- and z-positioners 20, 22 and 24 respectively. The head illustrated comprises an array of hollow pins 26, each connected to a fluid line. In one example, the head has a 1×8 array of pins with each pin 26 having its own fluid line 28 for aspiration (sucking) and dispensing (expulsion) of a cell colony to perform cell colony picking from a container followed by deposition of the cell colony sample into a well of a well plate 29 or other target location. It will be appreciated that multiple well plates 29 will normally be used, although only one is illustrated for the sake of simplicity. A grid of well plate receiving bays can be provided on the apparatus main bed. Automation of well plate handling may also be provided, for example using a "hotel" system, or a fully automated well plate feeder and stacker, as is known in the prior art. The head 18 is carried by the z-positioner, which is in turn carried by the y-positioner, which is carried by the x-positioner. The head also has mounted on one side a camera 19 for machine vision. The camera 19 may include a zoom objective lens, or swappable objective lenses, in order to provide different magnifications, and hence resolutions.

Alternatively, a further head-mounted camera (not shown) may be provided so that there are two cameras with different objective magnifications, one for low resolution, large area views and the other for small area, high resolution views. In use, the low resolution camera is used for mapping over the whole Petri dish or other container to identify the colony locations, and then the high resolution camera is used for imaging each colony. It will be understood that a similar procedure can be carried out with a single head-mounted camera with variable magnification.

Adjacent the head 18 the z-positioner may also have attached thereto a well plate gripper (not shown) to allow well plates to be moved around the main bed of the apparatus.

A single well plate 29 is illustrated on the main bed of the apparatus by way of example. The main bed may be provided with stations for well plates and colony dishes of various standard types.

After picked cell colonies have been dispensed into their wells, the pins need to be cleaned before they can be used to pick up further cell colonies so as to avoid cross-contamination. For the pin cleaning, a washing and drying station 2 is used. The washing part includes first and second baths 4 and 6. The drying part 8 consists of a cavity for blowing air onto the pins and preferably also halogen or other lamps. The lamps serve to sterilize and dry the pins by heating. The blower can assist drying, but if lamps are provided, serve principally to cool the pins after heating.

After completion of a run, the x- y- and z-positioners 18, 20 and 22 move the head over to the washing and drying station 2. The pins are lowered and dipped into the first wash bath 4, containing water, for example, or a water/bleach mixture. The first bath 4 may be fitted with upstanding brushes immersed in the cleaning liquid, in which case the x- and y-positioners are used to move the pins over the brushes in a rotary motion in the xy-plane. The pins are also preferably purged with a sterilizing solution, such as bleach. The head is then moved to the second bath 6, which contains, for example, ethanol for more cleaning. Ethanol is used in the last bath 6 in view of its volatility which assists the subsequent drying of the pins. It will be appreciated that the named cleansing agents are mentioned to give concrete examples. Other cleansing agents are sometimes used.

The head is then moved over to above the drying station 8. If provided, the halogen lamps are switched on at this point to heat the pins. An air blower is then switched on to dry the pins and/or to cool them to ambient temperature if they have been heated by the halogen lamp.

The main bed may also include other standard equipment such as a waste chute, a well plate delidder, well plate shakers, or well plate hotel. None of these is illustrated. The apparatus may also be provided with an automated well plate feeding and stacking mechanism and an automated cell colony dish feeding and stacking mechanism. Neither is shown.

Figure 2:
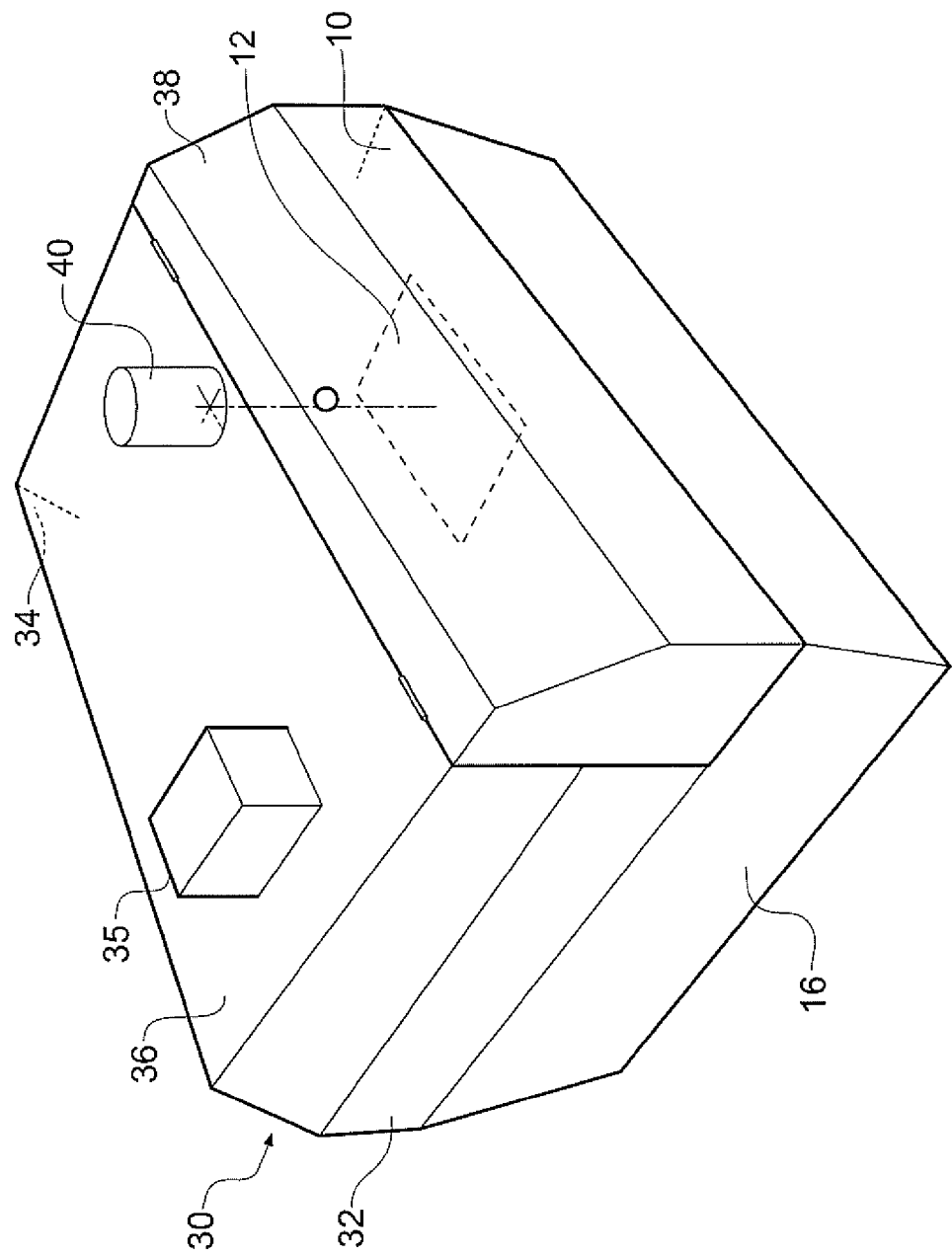
FIG. 2 is a perspective view of the apparatus.

FIG. 2 is a perspective view of the apparatus embodying the invention. In comparison to FIG. 1, the apparatus also shows the upper part of the machine. The upper part is principally formed of a light-tight and gas-tight cover 30 with two sides 32, a back 34 and a roof 36. A so-called high-efficiency particulate air (HEPA) filter unit 35 is also mounted on the roof 36. The working volume of the apparatus contained by the main bed 10 and the cover 30 can be kept in a controlled environment substantially free of contaminant particles by supplying filtered air into the working volume through the HEPA filter unit 35 and maintaining the working volume at slight overpressure so that unfiltered air from the surroundings is prevented from entering the working volume.

On the front side of the machine there is a hinged door 38 to provide access. Mounted in the roof, there is a detector unit 40 housing an array detector, in the form of a CCD chip, and associated imaging optics, in the form of an objective lens and an appropriate filter. The imaging optics are designed to have the upper surface of the light table plate as the imaging plane, or a slightly higher plane to take account of the usual thickness of the cell colony dish base. The CCD chip can be cooled with a Peltier cooler (not shown) to reduce noise. If a lower operating temperature is desired to further reduce noise, a cryogen such as liquid nitrogen could be used, for example with a closed cycle cryostat. The array detector need not be a CCD and could be any suitable two-dimensional array detector, such as a multi-channel plate (MCP). The array detector may be cooled, for example with a Peltier device or using a cryogen such as liquid nitrogen.

The detector unit 40 is contained in a cylindrical housing bolted upright on the roof of the machine so that the principal optical axis "O" of the detector unit is perpendicular to the plane of the main bed of the apparatus. Optical access to the light table below is provided by an aperture in the roof.

Figure 3:
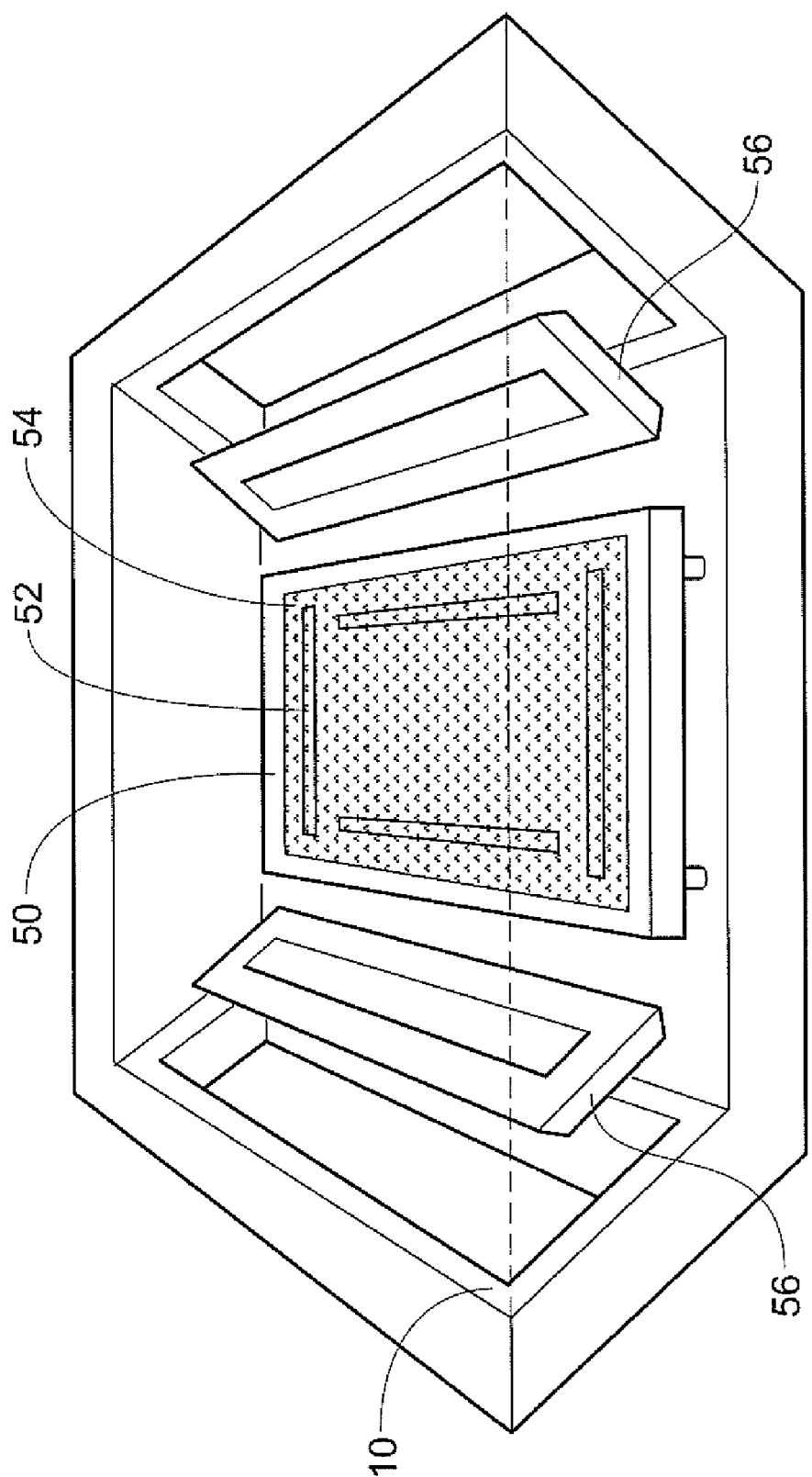
FIG. 3 shows features of the light table illumination system of the apparatus.

FIG. 3 shows features of the light table illumination system of the apparatus embodying the invention. The figure is a perspective view from one side of the machine from a position looking down onto and across the plane of the main bed of the machine, but with the main bed not shown. The plane of the main bed (and the light table plate) is marked with reference numeral 10. The main part of the illumination system is a source unit 50 which is rectangular in footprint having dimensions approximately matching those of the light table illumination plate (e.g. about 300×200 mm) and which has a thickness of approximately 20 mm. Arranged in the base of the source unit is a plurality of blue light emitting diodes (LEDs)

that emit at a nominal center wavelength of 473 nm. (In other embodiments different color LEDs could be used.) The LEDs are arranged in four banks 52 (dashed lines) with each bank being a packaged unit of 100 surface mounted LEDs with an integrated Fresnel lens. Alternatively, discrete LEDs could be used spread over the area of the source unit. Arranged over the LEDs covering the whole area of the source unit is a sheet of filter (not shown) followed by a sheet of holographic diffuser 54. The holographic diffuser is a sheet of plastic material with a microsculpted surface relief structure made by an embossing process using a holographically produced blank (see e.g. U.S. Pat. No. 5,534,386: Physical Optics Corporation [6]). The diffuser homogenizes the LED light output, so that the intensity distribution of light from the LEDs on the light table plate is equalized. Arranged on either side of the source unit there are strip light units 56 for providing white light illumination to the light table plate for contrast imaging.

Figure 4:
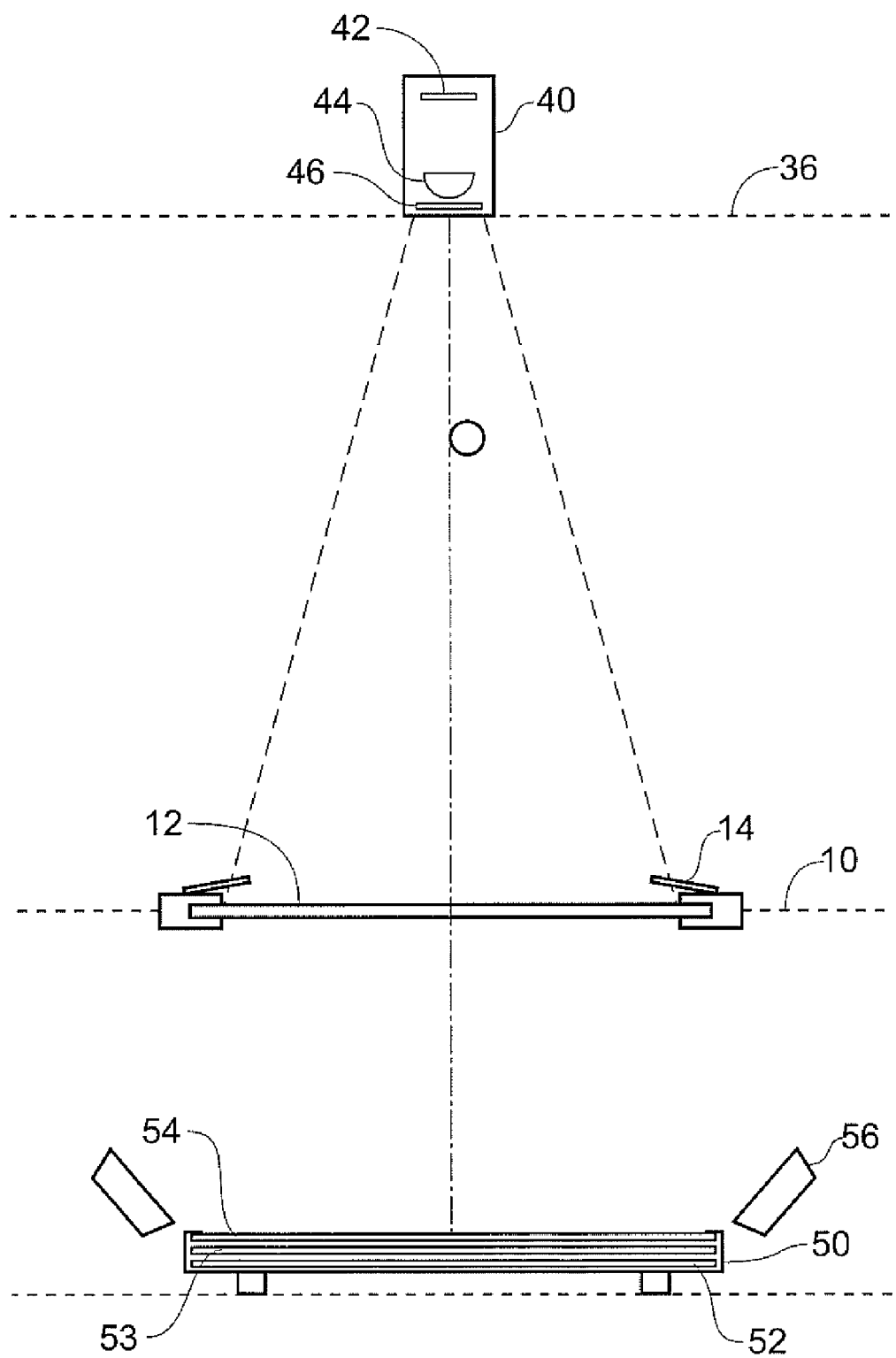
FIG. 4 is a schematic side view showing the optical design of the apparatus.

FIG. 4 is a schematic side view showing the optical design. At the top of the figure, the detector unit 40 can be seen mounted on the roof 36. The detector unit 40 contains a CCD chip 42 with associated collection optics 44 illustrated schematically as a single objective lens. It will be appreciated that any appropriate lens (or mirror) combination may be used in order to image the light table area onto the active surface of the CCD chip. The optical axis "O" of the detector unit 40 is also shown. The detector unit 40 also includes a filter 46. This is a bandpass filter for filtering out the LED output. A 620 nm center wavelength with 35 nm bandpass is selected for the blue LEDs mentioned above. It will be appreciated that in general an appropriate selection of bandpass or cutoff filter will be made having regard to the output response of the LEDs, and the excitation and emission bands of the fluorescent stain to be used. Moreover, in some applications, for example with contrast imaging, a filter may be dispensed with. In the middle of the figure, the light table plate 12 and dish clamps 14 are illustrated, with the light table plate 12 lying generally in the plane of the apparatus main bed 10. At the bottom of the figure, the light source unit 50 is shown with its LEDs 52, filter 53 and diffuser 54. The filter 53 is a bulk dyed band pass filter of the kind used for theatrical lighting which is blue in the present example where blue LEDs are used. The filter 53 is effective for removing undesired components of the LED output. Specifically in the case of blue LEDs it has been found that a small proportion of the LEDs malfunction by emitting wavelength components outside the blue into the green and red. A different color filter can be chosen depending on the output wavelengths of the LEDs used. The angled strip light units 56 are also evident.

A CCD exposure time of around 10 seconds to 3 minutes is usually sufficient to image cell colonies. The exposure time will depend on a number of factors, for example the type of stain used. One useful stain is trypan blue. The exposure time is proportional to illumination intensity, so that exposure time can be reduced by using more intense illumination from white light sources, lasers or LEDs.

Figure 5:
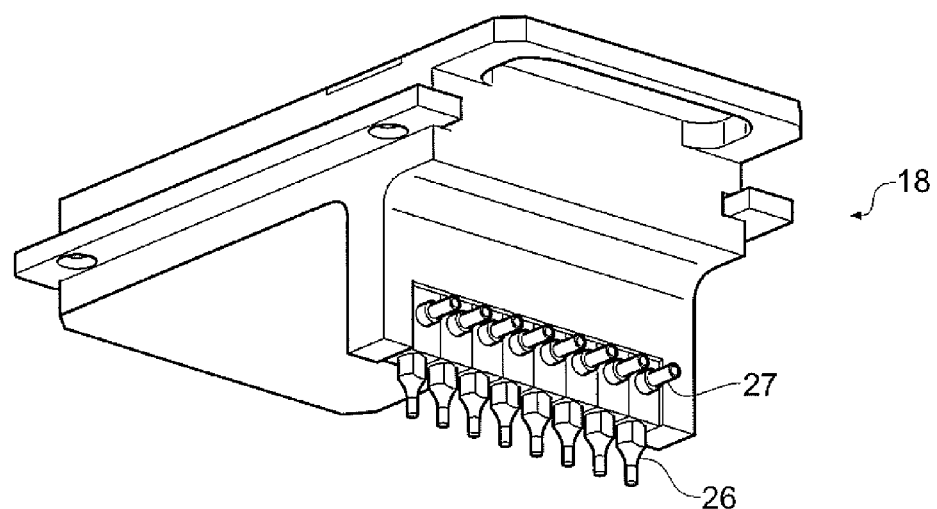
FIG. 5 is a perspective view of the head of the apparatus.

FIG. 5 is a perspective view showing a part of the head 18 in more detail. The end portions of the hollow pins 26 are visible protruding through the bottom of their housing parts. The hollow interior of the pins extends upwards and then through a right angle bend to emerge at stubs 27 for connecting flexible fluid lines (not shown in FIG. 5, but sketched in FIG. 1). It is also noted that the head 18 with pins can be removed as a single piece and autoclaved for sterilization.

Automated head swapping could also be provided as described in U.S. Ser. No. 10/144,763 by Ruddock, the contents of which is incorporated herein by reference. Various multiple head configurations are contemplated. For example, to improve speed, two heads similar to that shown in FIG. 5 could be provided. While one of these heads is being used, the other can be cleaned in an automated wash/dry station, thus eliminating dead time that would otherwise arise during head sterilization, as described in U.S. Ser. No. 10/298,948 by Elverd, Haslam and Ruddock, the contents of which is incorporated herein by reference. Another possibility is to provide a specialist imaging head for carrying the camera (or cameras). By providing a separate imaging head, this reduces the weight of the heads, thereby increasing the speed with which they can be scanned and avoiding overloading problems. This may be especially useful if the imaging head includes further parts, such as its own spectrometer or multiple cameras.

Figure 6:
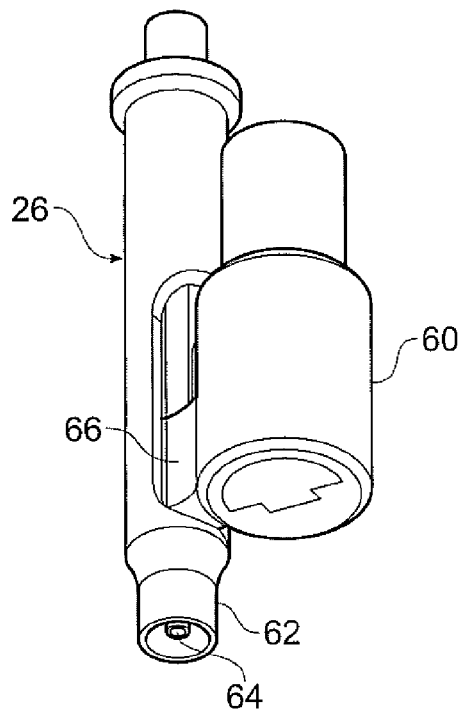
FIG. 6 is a perspective view of one pin of the head with associated agitation motor.

FIG. 6 is a perspective view of one of the pins 26 in more detail. As well as the pin an electric motor 60 is also shown fitted alongside the pin 26. The hollow pin 26 comprises both outer and inner pins 62 and 64, with the inner pin 64 arranged coaxially inside the outer pin 62. Both pins are made of stainless steel. The inner pin 62 forms the end of the fluid path that includes the flexible tubing. The electric motor 60 is connected to the inner pin 64 by a connecting rod 66 that is driven by a crank mounted on the motor 60. The motor thus drives the inner pin 62 so that it describes a rotary motion, with the motion being accommodated by bending of the inner pin 64.

In the present embodiment, the inner pin 64 has an inside diameter of 0.7 mm an outside diameter of 1.07 mm. The outer pin 62 is 35 mm long and has a 5 mm outer diameter, tapering to 4.2 mm at its end, and a 3.2 mm inner diameter. These dimensions are suitable for picking cell colonies of average size circa 0.5 mm.

Figure 7:
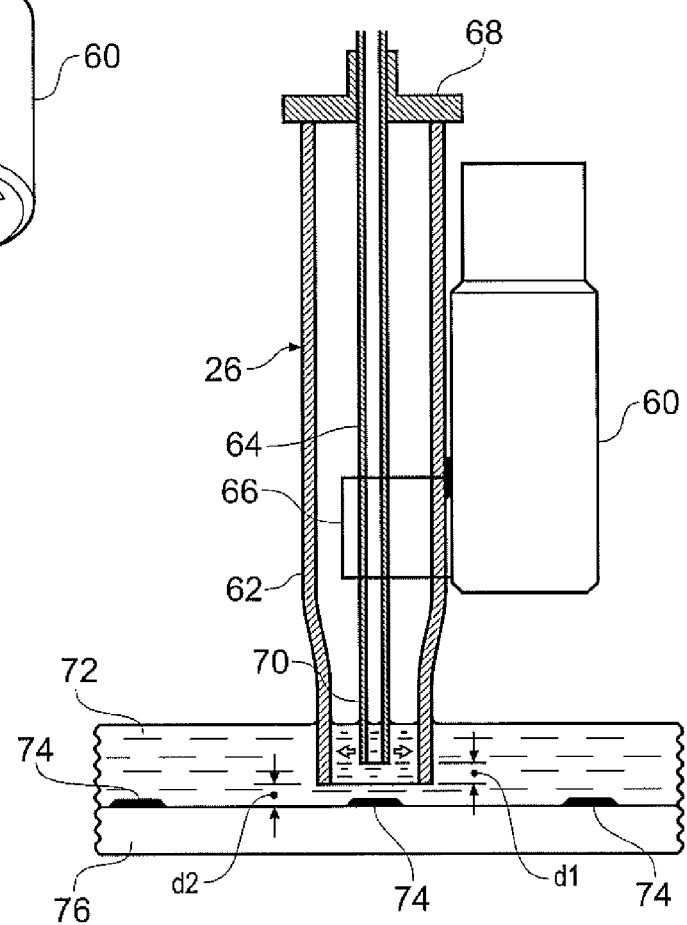
FIG. 7 is a schematic section of the pin and motor of FIG. 6 in use.

FIG. 7 is a schematic section of the pin 26 and motor 60 showing the pin in use for picking adherent cell colonies. The inner and outer pins 64 and 62 can be seen, as well as the motor 60 and connecting rod 66. As is shown, the end of the inner pin 64 is recessed axially inside the end of the outer pin 62 by a distance 'd1'. In the present embodiment values of d1=0.25–0.5 mm have been used. Other values in the range 0.1 to 2 mm could be suitable, depending on the relevant parameters such as average colony size and liquid viscosity. The figure shows the pin 26 lowered in position for picking an adherent cell colony 74. The pin 26 is lowered so that the distal end of the outer pin 62 is immersed in the liquid 72 and offset by a small amount 'd2' from the upper surface of the sample container base (substrate) 76 on which the cell colonies are grown. In the present embodiment, d2 is varied between about zero (i.e. butting against the plate 76) and 0.5 mm, although larger offsets could be contemplated, for example up to 2 mm. Values of zero (i.e. butting), 0.1 mm or 0.2 mm are usual. The pin 26 is also aligned with the cell colony 74 as determined by the xy coordinates of the colony determined by the image of the sample taken with the camera 40 and subsequent image processing.

In the position illustrated, the motor 60 is actuated to oscillate the end of the inner pin 64, thereby creating turbulence in the liquid 72. An oscillation frequency of around 100 Hz has been successfully used. Other frequencies would probably also work. The forces induced by this motion have been found sufficient to detach the cell colony and allow aspiration of the detached cell colony into the hollow pin, which as mentioned above forms the end of a capillary 70. The inner pin 64 is constrained by a flange 68 which fits into the top of the outer pin 62 and has a central through hole through which the inner pin 64 passes in a push fit.

In the case of non-adherent colonies held in a semi-solid growth medium, it will be understood that the colonies are not attached to the plate so there is no need to vibrate the pin.

Figure 8:
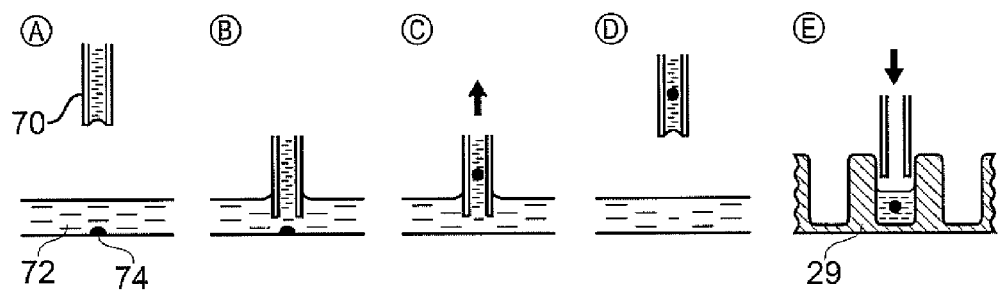
FIG. 8 is a series of schematic captions illustrating the main steps in picking a an adheent animal cell colony.

FIG. 8 is a series of schematic captions A-E illustrating the main steps in picking a targeted mammalian cell colony. In caption A, the pin 70 is being lowered over an adherent target colony 74 immersed in liquid 72 after alignment of the xy-coordinates. In caption B, the pin tip is immersed directly over the colony ready for carrying out the detachment process. Caption C shows the situation after the vibration-induced detachment in which aspiration is taking place. A column of liquid in which the colony is in suspension is drawn up into the pin by lowering of pressure in the pin. Caption D shows the situation after the pin has been raised out of the sample container. The colony is retained by a lower than atmospheric pressure being maintained in the pin. The head can then be moved over to a well plate for dispensing. Caption E shows the situation in which the end of the pin has been lowered into a well of a well plate, and the colony ejected from the pin by raising the pressure in the pin, thereby completing the cell picking operation.

The above description has taken the example of an adherent colony. It will be understood that when a colony is in suspension, a simplified form of the same process can be carried out with the steps associated with detaching an adherent colony being omitted. It will also be understood that some of the parts of the apparatus are redundant in the case of picking cell colonies from suspension and could be omitted if the machine did not need to have a capability for handling adherent colonies. For example, the outer pin could be omitted as well as the motor and associated drive parts.

Figure 9:
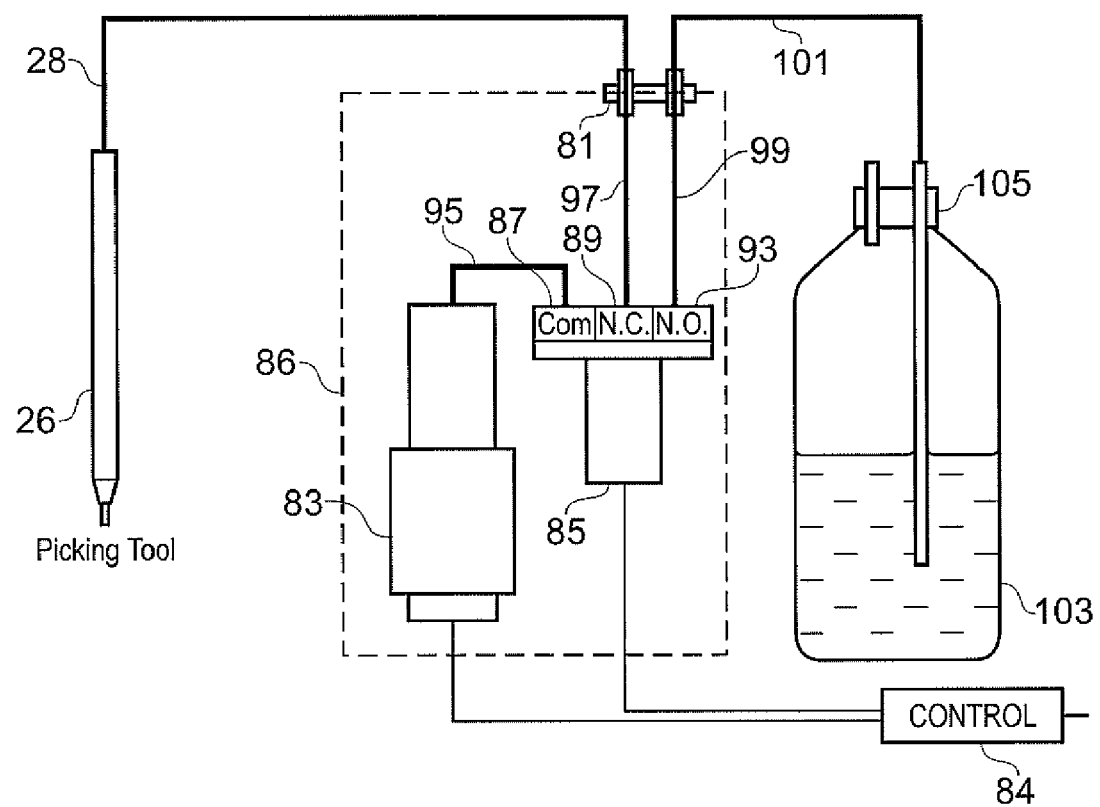
FIG. 9 is a schematic drawing of the fluidics elements of the apparatus.

FIG. 9 is a schematic drawing of the fluidics elements of the apparatus. One of the pins 26 is shown connected to its fluid line 28 made of flexible tubing which leads to a manifold 81 mounted on the housing of a fluidics unit 86. (The manifold 81 is used for receiving all the fluid lines 28, although only one is shown.) The manifold 81 also receives a further fluid line 101 from a liquid supply vessel 103 through a fluid line 101 which accesses the liquid in the supply vessel 103 through a sealed top flange 105. The liquid in the vessel 103 may be held under pressure. In the interior of the fluidics unit 86, the fluid supply is connected from the manifold 81 through a fluid line 99 to a normally open (N.O.) port 93 of a valve 85, and the other side of the fluid path leading to the pin 26 is connected from the manifold 81 through a fluid line 97 to a normally closed (N.C.) port 89 of the valve 85. The fluidics unit 86 also houses a pump 83, which is a reciprocating piston/cylinder pump which connects through a fluid line 95 to a common port (COM) 87 of the valve 85. The valve 85 and also the pump 83 are connected to a fluidics control unit 84 by electrical control lines. The fluidics control unit 84 is itself connected to and driven by a control computer (not shown in this figure).

In use, the valve 85 is controlled as follows. When the valve 85 is in its rest state with no inputs, the N.O. port 93 is open and the N.C. port 89 is closed. This connects the reciprocating pump 83 to the fluid vessel 103 so that it can draw liquid out of the reservoir by suitable downward motion of the pump piston in its cylinder. On the other hand, when the valve 85 is in its actuated state with an energizing input signal, the N.O. port 93 is closed and the N.C. port 89 is open. This connects the reciprocating pump 83 to the pin 26 allowing the liquid column in the fluid path formed by elements 26, 28, 97 and 95 to be moved in either direction by motion of the pump cylinder. This provides the fine control for the aspiration and expulsion of animal cell colonies shown schematically in FIG. 8 as described above. Raising of the piston also allows purging of the fluid path during cleaning. For cleaning, the fluid vessels can be swapped by hand. Alternatively, an automated switching between different fluid vessels can be provided using additional computer-controlled valves. On occasion, a pressurized gas canister could be used as a fluid vessel (e.g. for compressed gas cleaning), so the fluid vessels need not necessarily be liquid containing. It will be understood that the vessels 103 can be shared among multiple pins and there need not be a separate vessel 103 for each pin. Individual pumps could also be shared between two or more valves to reduce cost.

Figure 10:
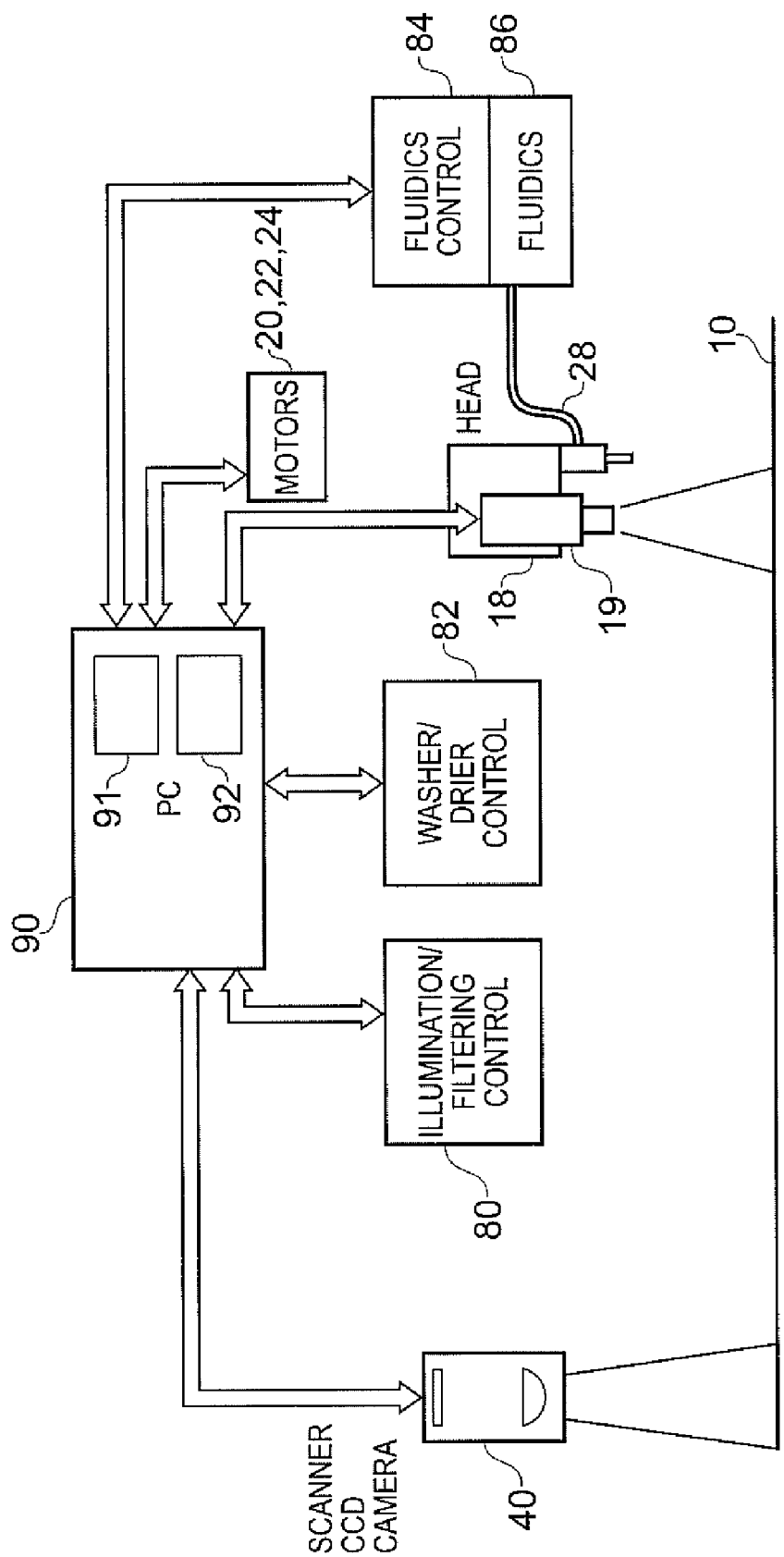
FIG. 10 is a block schematic diagram showing the control system of the apparatus.

FIG. 10 is a block schematic diagram showing the control system of the apparatus for coordinating the various components to perform the processes described above. A computer (PC 90) is used as the principal control component and is connected by electronic links using standard interfacing protocols to the various components that are part of the automated control system. The control is effected by control software 91 resident in the PC 90. Image processing software 92 is also resident in the PC 90 and linked to the control software 91. The detector unit 40 in the form of a CCD camera is connected to the PC 90 for receiving digital images captured by the camera. An illumination and filter controller 80 is connected to the PC 90. This controller is used to control the LEDs 52 and white light source unit 56 used to illuminate the light table plate 12 and also to select appropriate filter 46 from a motor driven filter wheel. A washer/drier controller 82 is connected to the PC 90 and used to control the blower and the halogen lamps of the drier. The positioners 20, 22, 24 for moving the head 18 are connected to the PC 90. The head-mounted camera 19 is connected to the PC 90 for receiving digital images captured by the head-mounted camera 19. These are used for aligning the pins of the head with the various parts of the washing and drying station 4, 6, 8, well plates 29, colonies etc. The fluid lines 70 are connected to the fluidics unit 86 which is controlled by the fluidics control unit 84 connected to the PC 90. The fluidics control unit 84 is used to control the pressure in the fluid lines to allow aspiration, retention and expulsion of liquid from the sample. The fluidics control unit 84 also controls the wash cycle of the pins and fluid lines, whereby cleaning fluid from the baths 4, 6 is aspirated and expelled from the ends of the pins during the cleaning cycle.

Figure 11:
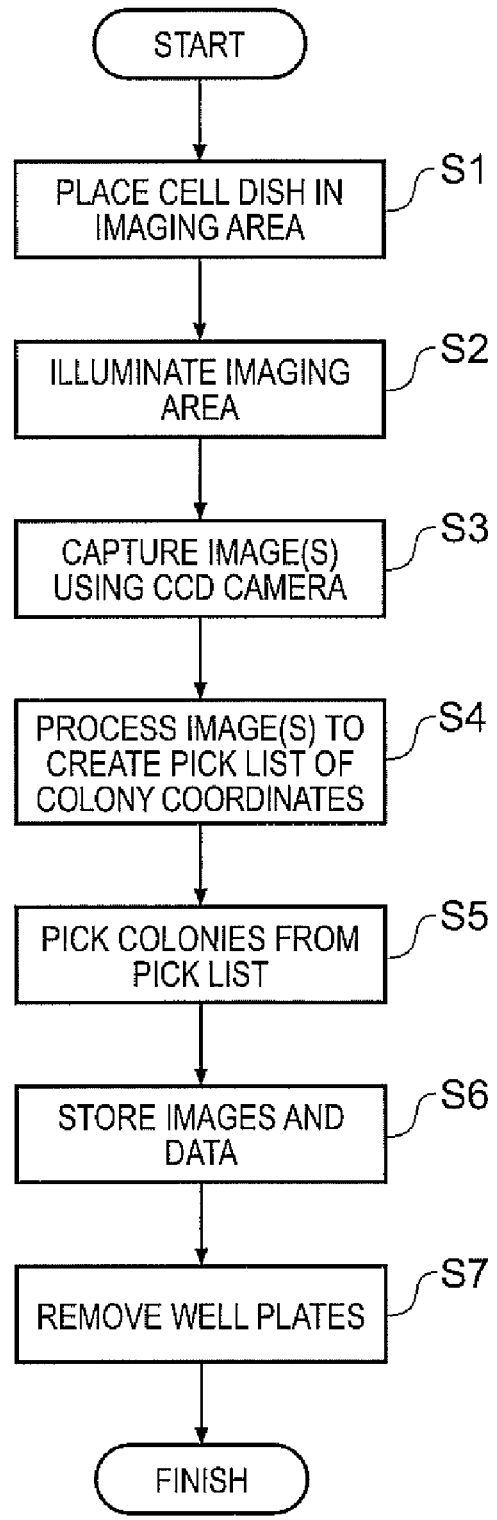
FIG. 11 is a flow diagram showing an example process carried out by the apparatus.

FIG. 11 is a flow diagram showing an example process carried out by the apparatus. The process has the following steps:

S1 Place cell dishes in imaging area, i.e. on light table plate 12

S2 Illuminate imaging area 12 using either the colored light source 52 (typically for detecting stained cell colonies using fluorescence) or the white light source 56 (typically for unstained colonies)

S3 Capture image(s) using CCD camera 40

S4 Perform software-based image analysis to detect cell colonies to pick—creating a "pick list"

S5 Assign the robotic apparatus to collect cell colonies from the pick list (described in more detail below)

S6 Store all images and data

S7 Remove well plates containing the picked colonies

Regarding steps S2 to S4, the cell colonies may be made visible using fluorescence. For example, a fluorescently labeled antibody may be used that binds to a protein of interest secreted from, expressed on the surface of, or contained within the cell colonies. During imaging of the fluorescence, the cell colonies appear as brightly emitting spots when illuminated with an appropriate excitation wavelength (e.g. with blue LEDs). Depletion of the fluorescent antibody in the immediate vicinity of the cell colonies also occurs which has the effect of producing an "inverse halo", i.e. a darker area around each bright colony which aids the image processing.

Alternatively, in the case of staining, the cell colonies are made visible by admixing a suitable stain into the suspension. It is however noted that it is possible to visualize many colonies without staining or fluorescence.

Figure 12:
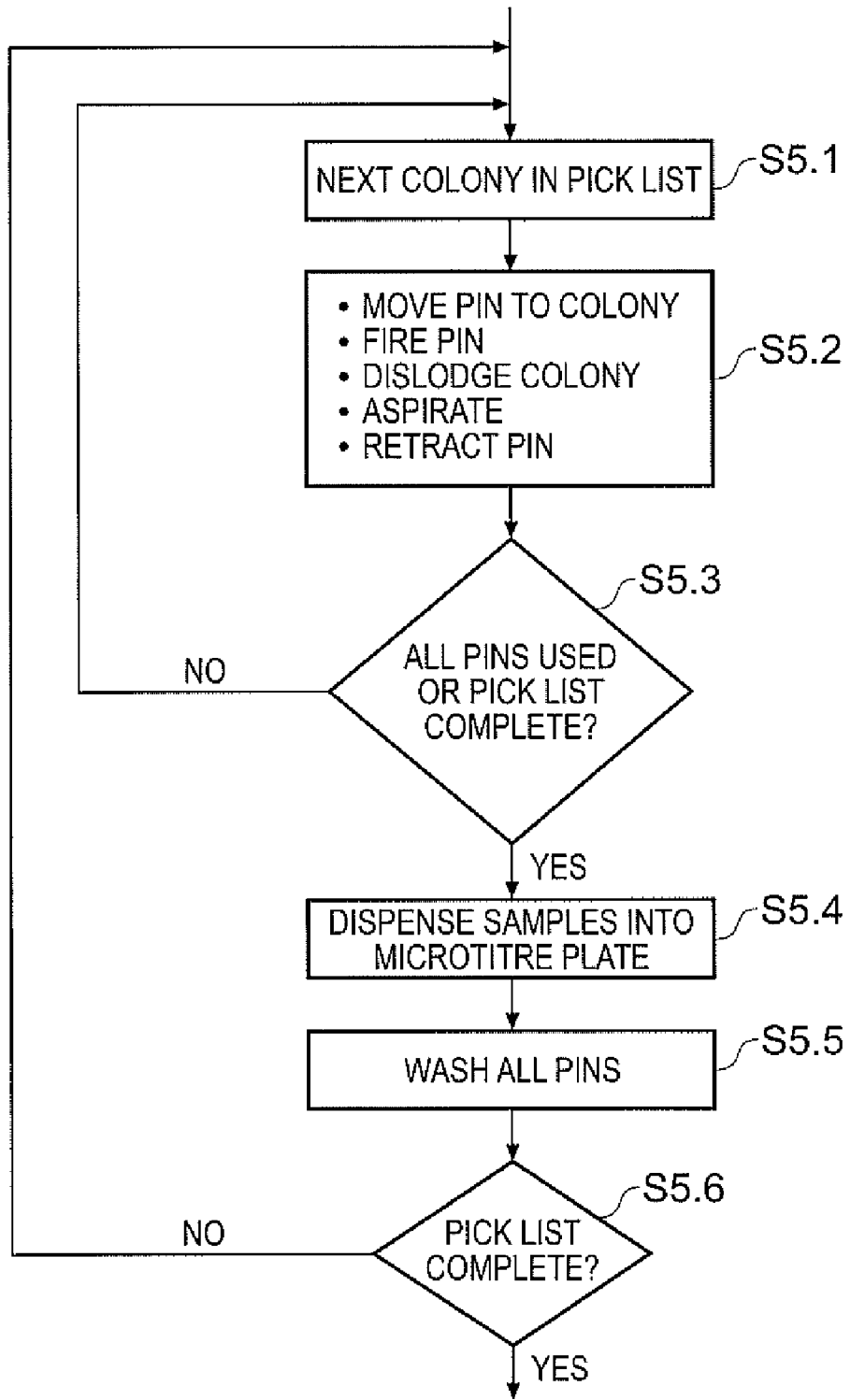
FIG. 12 is a flow diagram of the cell colony picking part of the process of FIG. 11.

FIG. 12 is a flow diagram showing in more detail Step S5, the cell colony picking part of the process. Step S5 of the process has the following sub-steps:

S5.1 Select pick list element for picking

S5.2 Move unused pin to above the assigned xy coordinate of the cell colony to be picked "Fire" (i.e. lower) pin to colony picking position with the end of the pin introduced into the medium over the target cell colony by offset 'd2'

For adhered colonies only—agitate pin end to dislodge target cell colony

Aspirate defined volume

Retract pin and retain sample while other pins are fired

S5.3 Unless all pins are used or all colonies in the pick list have been picked, repeat Step S5.2

S5.4 Move the head over to the well plate and align the pins with the wells—then dispense all the samples simultaneously into the well (microtitre) plate S5.5 Clean all the pins using the washer and drier station 2

S5.6 Unless all colonies in the pick list have been picked move the head back to the sample area and return to Step S5.1

This completes Step S5.

This concludes the description of the main embodiment. Various possible alternatives are now mentioned.

The aspiration has been described in terms of having a liquid column through the fluid lines and into the pins. An alternative would be to maintain a liquid column in the majority of each fluid line, but to have a plug of air or inert gas, such as helium or nitrogen, in the pin tip. Sample could be aspirated by drawing up the liquid column and air plug together, so that the air plug separates the sample liquid or semi-solid medium from the main body of the liquid column. The use of a gas plug offers improved sterility, since sample liquid is isolated from the main liquid column by the gas plug.

Alternative optical configurations are possible. For example, a laser source could be used, such as an ion laser, in place of light emitting diodes. The laser beam could be scanned over the light plate's lower surface. In this case a single channel detector could be used. Suitable ion lasers include argon ion and krypton ion sources. It will be appreciated that the beam scanning can be performed with appropriate scanning mirror optics. Emission wavelengths over a wide range could be used, for example 200 nm to 1.6 µm, or outside this range.

The apparatus can be used with a variety of optical based methods. Simple contrast imaging can be used, or more sophisticated spectroscopic methods based on absorbance, luminescence or Raman scattering. If more sophisticated spectral analysis is needed, such as for resonant Raman scattering, the collection optics may include a spectrometer or continuously tunable bandpass filter placed in front of the detector. In order to achieve significant absorbance changes, very high concentrations of dyes must be used and many cells are needed to achieve significant changes in optical density. Preferably, the optical based methods rely on fluorescence and/or luminescence which are more sensitive assay methods compared to absorbance.

It is also noted that although the main embodiment shows illumination of a light table from below, illumination from above could be used either instead of or in combination with illumination from below.

In some cases, the head-mounted camera (or cameras) could be used exclusively and the roof-mounted camera could then be dispensed with.

Luminescent substrates include, but are not limited to, luciferase, luciferin (Anal Biochem (1994) 219, 169-181)m aequorin (Methods Enzymol. (1978) 57, 271-291), and alkaline phosphatase (Clin. Chem (1996) 42, 1542-1546).

Fluorescent substrates can yield a very bright signal, which enables them to be easily detected at the single cell level. A preferred fluorescent protein is green fluorescent protein—such as a modified (e.g. mutated) GFP. By way of example only, GFP which may conjugated to one or more antibodies for the detection of a protein of interest.

The GFP of the jellyfish Aequorea victoria is a protein with an excitation maximum at 395 nm and an emission maximum at 510 nm and does not require an exogenous factor. The properties and uses of GFP for the study of gene expression and protein localization have been discussed in, for example, Nat Cell Biol (2002) 4, E15-20; Biochemistry (1974) 13, 2656-2662; Photochem. Photobiol. (1980) 31, 611-615; Science (1994) 263, 12501-12504; Curr. Biology (1995) 5, 635-642; and U.S. Pat. No. 5,491,084.

Accordingly, the apparatus of the present invention may be used with different fluorescent and non-fluorescent proteins and stains.

As further light emitting diode types become commercially available (e.g. in the ultraviolet), more groups can be provided so that the apparatus can be developed to provide a greater range of possible excitation wavelengths. The apparatus can also be made multi-functional by providing light emitting diodes of different types, for example a first group for outputting in a first wavelength band (e.g. blue) and a second group for outputting in a second wavelength band (e.g. green, red).

A variety of fluorescent stains are available emitting across the visible from ultraviolet, to blue, green, orange and red. It will be understood that the proposed design can be readily modified to use with any desired fluorescent stain/protein with suitable adaptation of the optical sources, filters and detector. Specifically, the invention can be applied to cy3 and cy5 stains available from Amersham Biosciences. Non-fluorescent stains to which the invention can be applied include trypan blue.

It will also be understood that although the term light emitting diode is used commonly in the art to describe only one type of light source based on diode emission, the term light emitting diodes is to be construed broadly in the claims of the present document to cover all forms of light emitting diode sources, including diode lasers, such as semiconductor diode lasers, and superluminescent diodes.

Ways in which a colony of interest can be identified using the apparatus are now described in more detail.

The automated process described herein may used to sort, pick or identify one or more cell colonies of interest based upon contrast imaging.

Therefore, the present invention may be used for identifying and analyzing biological molecules that may be present in a cell colony, including, for example, peptides, polypeptides, nucleic acids, and glycosylated and unglycosylated proteins (oligosaccharides, lipids and the like).

As will be appreciated by a person skilled in the art, a biological molecule, such as a protein of interest, may be detected in a variety of ways. By way of example only, the biological molecule may be detected as follows:

1. The expression system that is used to express the protein of interest may be one which causes the protein of interest to be secreted from the cell colony into the surrounding medium. If the expressed protein is secreted into the culture medium, then typically the expression vector will contain a suitable signal sequence that directs the secretion of the protein to the culture medium. A fluorescent antibody, for example, that is specific for the protein of interest may then be used for the subsequent identification of cell colonies expressing the protein of interest.

2. The expression system that is used to express the protein of interest may be one which results in the expression of the protein of interest on the surface of a cell—such as the cell membrane. As will be understood by those of skill in the art, vectors—such as expression vectors—containing coding sequences may be designed with signal sequences which direct secretion of the coding sequences through a particular cell membrane. A fluorescent antibody, for example, may then be used for the subsequent identification of cell colonies expressing the protein of interest.

3. The cell colony could be made permeable using a cell permeablization agent, such that a fluorescent antibody for example, can enter the cell colony and associate with the protein of interest, whilst still maintaining the viability of the cell colony.

4. The cell colony may comprise an expression vector in which a protein of interest is fused to a reporter or a 'tag'—such as GFP. In this manner, expression of the protein of interest also results in the expression of the reporter which provides for the identification of the cell colony. The unique tag sequence is added to the nucleotide sequence encoding the protein by recombinant DNA techniques, creating a protein that can be recognized by an antibody specific for the tag peptide, for example. A wide variety of reporters may be used in accordance with the present invention with preferred reporters providing conveniently detectable signals (e.g. by fluorescence). By way of example, a reporter gene may encode an enzyme which catalyses a reaction, which alters light absorption properties. Examples of reporter molecules include but are not limited to β-galactosidase, invertase, green fluorescent protein, luciferase, chloramphenicol, acetyltransferase, β-glucuronidase, exo-glucanase and glucoamylase. For example, fluorescently labeled biomolecules specifically synthesized with particular chemical properties of binding or association may be used as fluorescent reporter molecules. Fluorescently labeled antibodies are particularly useful reporter molecules due to their high degree of specificity for attaching to a single molecular target in a mixture of molecules as complex as a cell, tissue or extract of either.

A wide variety of ways to measure fluorescence are available. For example, some fluorescent reporter molecules exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements. Multispectral imaging could also be used.

APPLICATIONS EXAMPLES

Some specific examples of how the apparatus of the invention may be used are now given.

Selection of Cells for Biopharmaceutical Production

The present invention may also be suited to the automated sorting of cell colonies which express or secrete enhanced levels of a protein of interest. In a preferred embodiment, the protein of interest is a biopharmaceutical protein, such as protein that is useful in the treatment or diagnosis of disease.

Such cells may be detected according to, for example, the brightness of the fluorescence of the cell colony which will correlate with the amount of protein that is expressed. The brightest cell colonies may then be picked for further analysis/processing.

As described above, the present invention might also be suited to the recovery of cell colonies producing membrane and secreted proteins.

Stem Cells

Differentiation is a process whereby structures and functions of cells are progressively committed to give rise to more specialized cells. Therefore, as the cells become more committed, they become more specialized. In the majority of mammalian cell types, cell differentiation is a one-way process leading ultimately to terminally differentiated cells. However, although some cell types persist throughout life without dividing and without being replaced, many cell types do continue to divide during the lifetime of the organism and undergo renewal. This may be by simple division or, as in the case of cells—such as haematopoietic cells and epidermal cells—by division of relatively undifferentiated stem cells followed by commitment of one of the daughter cells to a program of subsequent irreversible differentiation.

Since the present invention is particularly suited for the identification of cells based upon differences in cell size, shape and/or replication rate, this may be used to identity and/or isolate one or more stem cells once they have differentiated into a given cell type.

RNAi

Post-transcriptional gene silencing (PTGS) mediated by double-stranded RNA (dsRNA) is a conserved cellular defense mechanism for controlling the expression of foreign genes. It is thought that the random integration of elements such as transposons or viruses causes the expression of dsRNA, which activates sequence-specific degradation of homologous single-stranded mRNA or viral genomic RNA. The silencing effect is known as RNA interference (RNAi). The mechanism of RNAi involves the processing of long dsRNAs into duplexes of 21-25 nucleotide (nt) RNAs. These products are called small interfering or silencing RNAs (siRNAs) which are the sequence-specific mediators of mRNA degradation.

In differentiated mammalian cells dsRNA>30 bp has been found to activate the interferon response leading to shut-down of protein synthesis and non-specific mRNA degradation. However this response can be bypassed by using 21 nt siRNA duplexes allowing gene function to be analyzed in cultured mammalian cells.

In mammals, RNAi can be triggered by delivering either short dsRNA molecules (siRNAs) directly into the cell, or by delivering DNA constructs that produce the dsRNA within the cell.

The process and apparatus can be used to identify and pick cells with an altered phenotype for further analysis, since the RNAi induces morphological changes in the cells.

Cell Transformation Assays

Differences between transformed and non transformed cells may also be detected in accordance with the present invention.

Such assays may be used to assay for the transforming abilities of viruses or chemicals, for example.

Such assays also represent a method for assaying changes consistent with tumorigenesis without knowing the genetic nature of the damage giving rise to the change. After plating at low density, transformed cells, which have an altered phenotype, may be identified using morphological criteria, which is identifiable in an automated process using the imaging capability of the apparatus of the invention.

Cell transformation assays therefore test for genetic alteration that gives rise to an altered phenotype that is readily identified by the morphological appearance of the transformed cells.

Recovery of Viruses

The presence of a virus often gives rise to morphological changes in a host cell. Any detectable changes in the host cell due to infection are known as a cytopathic effect. Cytopathic effects may consist of cell rounding, disorientation, swelling or shrinking, death, detachment from the surface, etc.

The cytopathic effects produced by different viruses depend on the virus and the cells on which it is grown. This can be used in the clinical virology laboratory to aid in identification of a virus isolate.

Such cytopathic effects may alter the morphology of the cell which can be detected using the automated process described herein.

Transfection of Genes

In general, the insertion of a gene into a cell requires a dominant selective marker, such as neomycin resistance. The high efficiency of an automated system described here could make such a marker redundant as cells could be plated at limiting dilutions and colonies picked for further analysis.

Immortalization of Cells

Transformation with chemicals or viruses can induce an immortal phenotype. The apparatus and process described herein will allow such cells to be selected.

Selection of Cell Clones Producing Post Translational Modified Proteins

Therapeutic proteins, such a erythroprotein or tissue plasminogen activator, owe their serum half lives to sugar residues on the protein. Clones of cells producing a desired modification can be detected with a labeled lectin and then picked.

It will be appreciated that although particular embodiments of the invention have been described, many modifications/additions and/or substitutions may be made within the spirit and scope of the present invention.

REFERENCES

[1] U.S. Pat. No. 6,198,107: Clare Chemical Research, Inc.
[2] JP 07-260742: Sanyo Electric Co Ltd.
[3] WO 98/23950: Oxford Glycosciences (UK) Ltd.
[4] U.S. Pat. No. 5,587,062: Shimadzu Corporation
[5] WO 99/051977: Max-Planck-Gesellschaft zur Förderung der Wissenschaften
[6] U.S. Pat. No. 5,534,386: Physical Optics Corporation

What is claimed is:

1. A method for selecting animal cell colonies producing post-translationally modified proteins using an apparatus comprising machine vision, the method comprising:
   a) placing a sample container including a plurality of animal cell colonies producing post-translationally modified proteins held in a medium onto the apparatus;
   b) contacting the animal cell colonies with labeled lectin;
   c) identifying locations of animal cell colonies in the sample container producing post-translationally modified proteins using machine vision and image processing;
   d) selecting one or more of the animal cell colonies based on their production of post-translationally modified proteins;
   e) providing a picking head comprising at least one hollow pin, the picking head being movable over the apparatus using positioning motors;
   f) aligning the picking head, wherein the picking head includes a hollow pin, and wherein said one animal cell colony to be picked has a size smaller than an inside diameter of said hollow pin with the sample container;
   g) picking one of the selected animal cell colonies by aligning one of the at least one hollow pins with one of the animal cell colony locations, introducing a distal end of said hollow pin into the medium, and aspirating the animal cell colony at that location into said hollow pin, wherein said animal cell colony to be picked has a size smaller than an inside diameter of said hollow pin;
   h) placing a dispensing container onto the apparatus; and
   i) dispensing the picked animal cell colony by aligning the picking head with the dispensing container and expelling the picked animal cell colony into the dispensing container.

2. The method according to claim 1, wherein the picking step comprises repeating the aligning and aspirating steps for the at least one hollow pin to pick multiple ones of the colonies.

3. The method according to claim 1, wherein the at least one hollow pin comprises a plurality of hollow pins.

4. The method according to claim 3, wherein the dispensing container comprises an array of wells separated by a characteristic spacing and the hollow pins are also arranged with the characteristic spacing so that the expelling step can be performed in parallel for all the hollow pins.

5. The method according to claim 1, wherein the colonies are adhered to the sample container, and wherein after the introducing step the distal end of the pin is agitated relative to the sample container so as to detach the colony at that location prior to performing the aspirating step.

6. The method according to claim 1, wherein the introducing step comprises moving said hollow pin to a colony picking position in which the distal end of said hollow pin is immersed in the medium and offset from a base of the sample container by an offset distance, and the aspirating step is carried out at said colony picking position.

7. The method of claim 6, wherein the offset distance is in a range between 0.1 mm and 4.0 mm.

8. The method of claim 6, wherein the offset distance is in a range between 0.25 mm and 1.0 mm.

9. The method according to claim 1, comprising: (i) using said machine vision to capture an image of the sample; (ii) performing analysis of the image with said image processing to detect those colonies to pick, thereby creating a pick list of target colonies; and (iii) assigning the apparatus to collect the target colonies from the pick list, wherein the target colonies are picked by repeatedly performing said aligning, picking and dispensing steps.

10. The method according to claim 1, wherein the medium is a semi-solid or liquid medium.

11. The method according to claim 1, wherein the colonies are stained with a contrast enhancing agent to assist the image processing.

12. The method according to claim 1, wherein the colonies are stained with a fluorescent agent to assist the image processing.

13. The method according to claim 1, wherein the animal cell colonies comprise or express a biological molecule of interest.

14. The method according to claim 13, wherein the biological molecule of interest is a therapeutic protein.

15. The method according to claim 14, wherein the therapeutic protein is erythropoietin or tissue plasminogen activator.

16. A method for selecting animal cell colonies producing post-translationally modified proteins using an apparatus comprising machine vision and image processing, the method comprising:
   a) providing a plurality of animal cell colonies in a medium;
   b) contacting the animal cell colonies with labeled lectin;
   c) identifying locations of animal cell colonies producing post-translationally modified proteins bound by the labeled lectin, using the machine vision and image processing of the apparatus;
   d) selecting one or more of the animal cell colonies producing post-translationally modified proteins;
   e) providing a picking head that is alignable with the locations using positioning motors; and
   f) picking one of the selected animal cells colonies by aspiration into the picking head.

17. The method according to claim 16, wherein the medium is held in a sample container, further comprising a step of moving said hollow pin to a colony picking position in which a distal end of said hollow pin is immersed in the medium and offset from a base of the sample container by an offset distance, and wherein the step of picking includes a step of aspirating carried out at said colony picking position.

18. The method according to claim 17, wherein the offset distance is in a range between 0.25 mm and 1.0 mm.

19. The method according to claim 16, wherein the animal cell colonies express erythropoietin or tissue plasminogen activator.

* * * * *